United States Patent [19]
Giele

[11] Patent Number: 5,456,707
[45] Date of Patent: Oct. 10, 1995

[54] PACING LEAD WITH IMPROVED TORSION CHARACTERISTICS

[75] Inventor: Vincent Giele, LG Dieren, Netherlands

[73] Assignee: Vitatron Medical BV, Dieren, Netherlands

[21] Appl. No.: 141,874

[22] Filed: Oct. 22, 1993

[51] Int. Cl.⁶ .................................................... A61N 1/04
[52] U.S. Cl. .......................................... 607/127; 607/122
[58] Field of Search ........................... 128/642; 607/122, 607/125–128

[56] References Cited

U.S. PATENT DOCUMENTS

| | | |
|---|---|---|
| 4,046,151 | 9/1977 | Rose . |
| 4,135,518 | 1/1979 | Dutcher .................................. 128/642 |
| 4,463,765 | 8/1984 | Gold . |
| 4,493,329 | 1/1985 | Crawford et al. ....................... 607/125 |
| 4,920,980 | 1/1990 | Jackowski ............................. 128/642 X |
| 5,003,992 | 4/1991 | Holleman et al. .................. 128/642 X |
| 5,056,516 | 10/1991 | Spehr . |

Primary Examiner—William E. Kamm
Assistant Examiner—Jeffrey R. Jastrzab
Attorney, Agent, or Firm—Woodcock Washburn Kurtz Mackiewicz & Norris

[57] ABSTRACT

A pacing lead for connection between a pacemaker and a patient's heart, the pacing lead having conventional flexibility through proximal and distal lengths, and increased stiffness through an intermediate or middle length. The increased stiffness of the intermediate distance provides enhanced torsion characteristics, permitting easier and more accurate manipulation of the distal end of the lead. Increased stiffness of the intermediate length can be provided by a shrink tubing over the intermediate section of the lead coil, by a coating which is sprayed onto the coil to restrict its flexibility, or a tubing which is interference fit within the ID of the lead outer casing so as to constrain variation of the coil and increased stiffness. In each embodiment the friction between the coil and the outer casing is reduced through the intermediate middle length, so as to reduce the amount of twisting that is transmitted through to the tube casing, thereby enabling more efficient rotation of the anchor mechanism at the distal end of the lead.

16 Claims, 2 Drawing Sheets

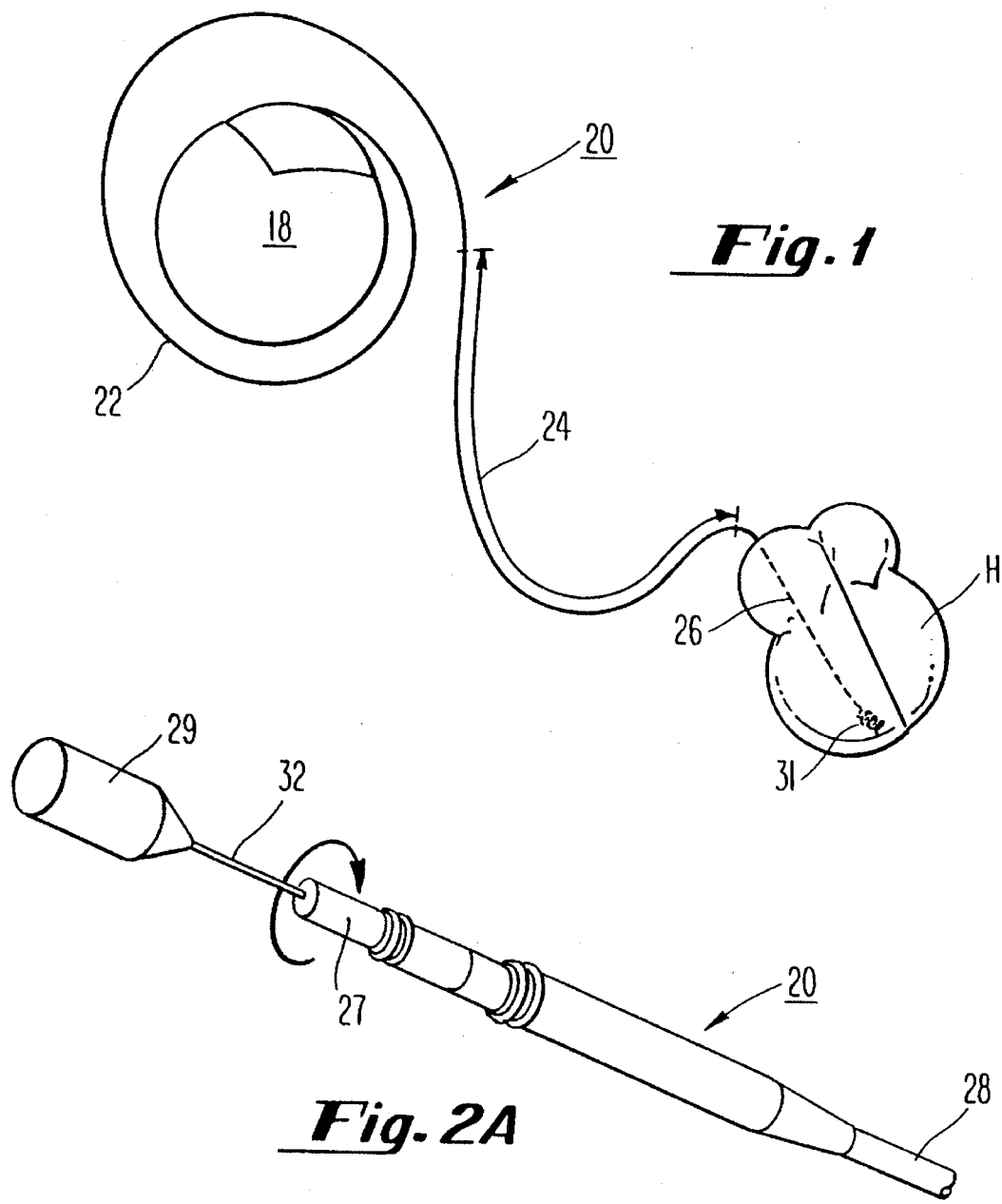
Fig. 1
Fig. 2A
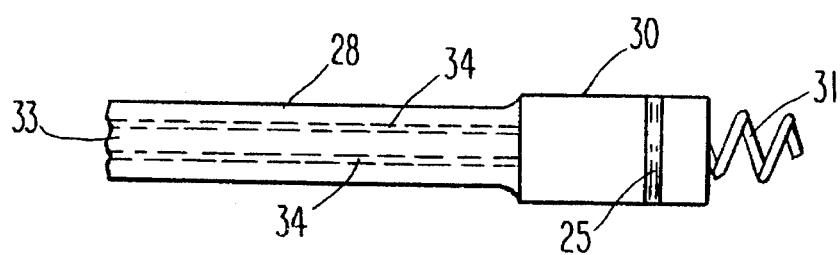
Fig. 2B

PACING LEAD WITH IMPROVED TORSION CHARACTERISTICS

FIELD OF THE INVENTION

This invention relates to pacing leads and, more particularly, to a pacing lead having a distal element such as an anchoring mechanism which is movable by applying a rotating force at the proximal end of the pacing lead.

BACKGROUND OF THE INVENTION

Endocardial pacing leads having fixation structures at or near the distal tip are well known in the art and widely used. Some leads employ passive fixation or anchor structures, such as in the use of tines. However, it is also popular to use an active anchoring element, such as a retractable helical screw-in element, which is activated by the physician. Likewise, even tines can be designed to be retractable, and changed from a retracted state where they lie essentially along the circumference of the lead to an active or extended state. The activation or movement of such an anchor element can be achieved by applying a rotating, or torsional force to the coil element that runs the length of the lead, the rotational movement being transmitted the length of the lead to rotate the anchor element in one direction or another. Thus, the user rotates the connector pin on the proximal end of the lead, which pin in turn is connected to the coil, the coil being connected to the helix or anchor mechanism at the distal end of the lead.

In practice, the conductor coil through which the torsion is transmitted the full length of the lead has rather bad torsion characteristics. This is because the inner coil is generally designed to be flexible, to meet other requirements. Also, friction between the inner wall of the lead casing and the coil can be very high, especially when the tubing, or tubing, is made of a material such as silicone rubber. The result of such high friction is that torque transmitted to the coil is in turn carried also by the casing, such that a lot of the torsion is taken up in twisting the entire lead instead of being transmitted directly through to the distal end. In practice, the user may have a very uncontrolled feeling, and may be required to rotate the connector pin eight times or more in order to rotate the anchor mechanism one time.

In order to achieve good torsion, the ideal situation would be that the lead coil has no flexibility, such that it transmits all of the torsion (torque) inputted at the proximal end through to the element at the distal end. Also, in order to optimize transmission of torsion there would ideally be no friction between the coil and the inner wall of the tubing, so that none of the rotation is transmitted through to the tubing. Of course, the problem that has always faced the art area is that the coil needs to be flexible for other purposes. Also, since it is desirable to minimize the diameter of the lead, it is difficult to reduce friction between the coil and the inner wall of the outer casing.

Heretofore, there has not been a solution in the pacer lead area to the problem of providing a lead with the required flexibility, but yet optimizing the ability of the lead to transmit torque through to the distal end. Leads are known which have different stiffening characteristics along their lengths. Thus, in U.S. Pat. No. 4,493,329, Crawford et al., stiffening is provided to the J portion of an atrial lead. Also, in U.S. Pat. No. 4,135,518, Dutcher, assigned to Medtronic, Inc., a section adjacent to the distal electrode is provided with a greater flexibility, while the remainder of the lead is relatively stiffer. The purpose of this second design is to provide a first segment of the lead which is capable of bearing an axial mechanical force, and a second segment which is more flexible and incapable of sustaining axial mechanical force. However, this lead design does not provide the type of improved torsion characteristics as are desired to overcome the prior art problems as set forth above.

SUMMARY OF THE INVENTION

In order to provide a solution to the above problem, there is provided a pacing lead having increased stiffness and reduced friction in the mid-section of the lead, such that a first length of the lead at the proximal end and a second length of the lead at the distal end are characterized by a desired flexibility, while the mid-section of intermediate length, is characterized by an increased ability to transmit torque, or torsion. In practice, for a ventricular pacing lead of approximately 60 cm, the mid-section, spaced substantially equally between the proximal and distal ends, is about 32 cm in length. For an atrial pacing lead of about 52 cm, the mid-section is about 30 cm. In a first embodiment, (TEFLON)® shrink tubing is placed over the coil throughout only the intermediate length, to constrict the coil and reduce its flexibility, thereby increasing stiffness. The teflon shrink tubing also provides an improved, or lesser friction with the inside of the lead casing. Also, the inner wall of the lead casing may be suitably coated with a coating which reduces the coil-casing friction throughout any portion or the entire length of the lead.

In another embodiment, a (TEFLON)® coating is sprayed onto the outside of the conducting coil. For example, a five filar coil is used, and a mandril is placed in the lumen of the coil during coating so that the lumen will not be filled during the coating procedure. The thin, flexible coating adheres to the separate filars, holding them together and increasing resistance against coil diameter deformation, thus increasing stiffness and capacity to transmit torque. Since this principle works in both torque directions, a stylet is not needed, but still may be used.

In another embodiment, a thin tubing of a material such as polyamide is interference fit with the inner diameter (ID) of the tube casing, providing minimum clearance with the coil, throughout the length of the pacing lead. This embodiment may be further enhanced by using a stylet having an OD which is about the same as the coil ID.

BRIEF DESCRIPTION OF THE DRAWINGS

FIG. 1 is a diagrammatic representation of a pacing system employing a pacing lead in accordance with this invention.

FIG. 2A is a perspective representation of the proximal end of a pacing lead in accordance with this invention, also showing a stylet introduced into the lead. FIG. 2B is a diagrammatic representation of the distal end of a pacing lead in accordance with this invention and having a helical retractable screw-in fixation element.

DESCRIPTION OF THE PREFERRED EMBODIMENTS

Figure 3:
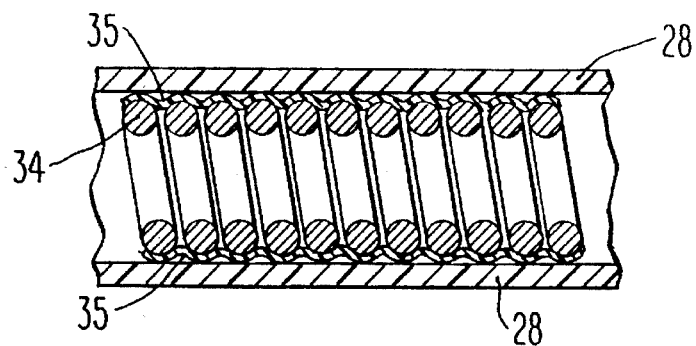
FIG. 3 is a cross-sectional view of a lead in accordance with this invention, having a (TEFLON)® shrink tubing placed around the coil through an intermediate length of the lead.

Referring now to FIG. 1, there is shown a diagrammatic illustration of the pacing lead 20 of this invention. The pacing system comprises a pacemaker 18, designed to generate and deliver pace stimulus pulses and to receive signals sensed from the patient's heart. The pacer communicates with the heart H through lead 20. A first proximal length 22 of the lead has usual and conventional lead characteristics, and is appropriately flexible. This flexibility is necessary in order to conveniently and easily run the lead from the terminal block of the pacer toward the patient's heart. A distal length 26 of the heart likewise has conventional flexibility, and covers a distance sufficient to reach from outside of the heart to the inner wall of the ventricle where the pacer electrode is to be fixed. As is known, this portion of the lead must be flexible, and length 26 has normal lead characteristics. The center, or intermediate length 24 of the lead is illustrated by an arrow and is defined as that length between the proximal length 22 and the distal length 26. In a ventricular pacing lead of about 60 cm, length 24 is typically in the range of 28–36 cm; length 22 is in the range of 10–15 cm; and length 26 is in the range of 10–15 cm. In accordance with this invention, length 24 is modified as compared to prior art leads, to provide it with improved torsion characteristics, so as to permit manipulation of an element at the distal tip of the pacing lead.

Referring to FIGS. 2A and 2B, there are shown perspective views of the proximal and distal ends of lead 20. The primary length of the lead has a conventional casing or tubing 28, which contains within it a conductor 34 which extends the length of the lead, to provide electrical connection between pacer 18 and a distal electrode. The conductor is electrically connected to proximal pin 27, which pin is designed to interconnect with the pacemaker in a known fashion. As indicated by the arrow, rotational force can be applied to pin 27, which is transmitted by the coil 34 to the distal end of the lead. Also shown in FIG. 2A is a stylet 32 which is manipulated by manipulating element 29, in a known fashion.

Referring to FIG. 2B, there is shown a diagrammatic representation of a typical distal end of a helical "screw-in" electrode. As shown, the tubing 28 terminates at the distal end of the lead in a cylindrical piece 30, which is connected to the coil 34 that runs the length of the lead. Coil 34 thus also provides a mechanical connection such that when the coil is rotated, cylinder 30 is likewise rotated and carries with it the helix 31. A lumen 33 extends the length of the lead, within the coil 34. Although the invention is illustrated with a simple version of pacing lead wherein element 31 is both the electrode and the fixation element, or anchor, it is to be understood that helix 31 may be solely a fixation element, and one or more separate electrode elements may be provided at the distal end of the lead, as illustrated at 25. Likewise, the invention may incorporate other types of anchor elements.

Referring now to FIG. 3, a first embodiment of the invention is illustrated. In this embodiment, a shrink tubing 35, preferably made of (TEFLON)®, is heat shrunk onto the mid-section of the coil, i.e., along the length 24. The shrinking action causes the coil to lose flexibility along the length of tube 35, such that it increases in stiffness. Further, the property of the Teflon is such as to improve (reduce) the friction between the coil and the ID of the coating 28. Thus, with the embodiment of FIG. 3, the coil itself is stiffer through intermediate distance 24, and the rotation of the coil is not so easily transmitted to the casing 28. By this means, an increased stiffness and improved torsion characteristic is imparted to a substantial length of the pacing lead, while maintaining the desired and necessary flexibility at the distal and proximal ends.

Figure 4:
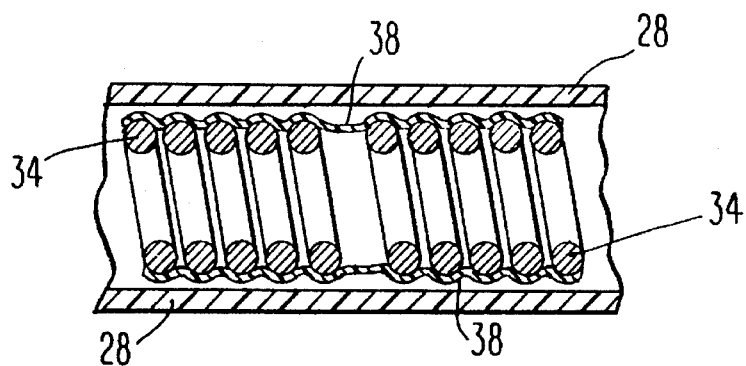
FIG. 4 is a diagrammatic cross-sectional view of a portion of a five filar wire coil, with a coating sprayed on the coil wires in accordance with another embodiment of this invention.

Referring now to FIG. 4, there is shown a diagrammatic cross-section of a portion of distance 24, embracing a different embodiment of the invention. In this embodiment, a sprayed coating, or layer 38, is adhered to the outside of the coil 34. For a five filar wire, as illustrated, the sprayed layer adheres to the separate filars, and provides the increased rigidity that is desired. As with the first embodiment of FIG. 3, the coating 38 likewise improves the friction between the coil and the tube casing, i.e., reduces the friction. In the step of applying the coating, it is desirable to place a mandril in the lumen 33 of the coil, so that the lumen will not be filled during the coating process.

Figure 5:
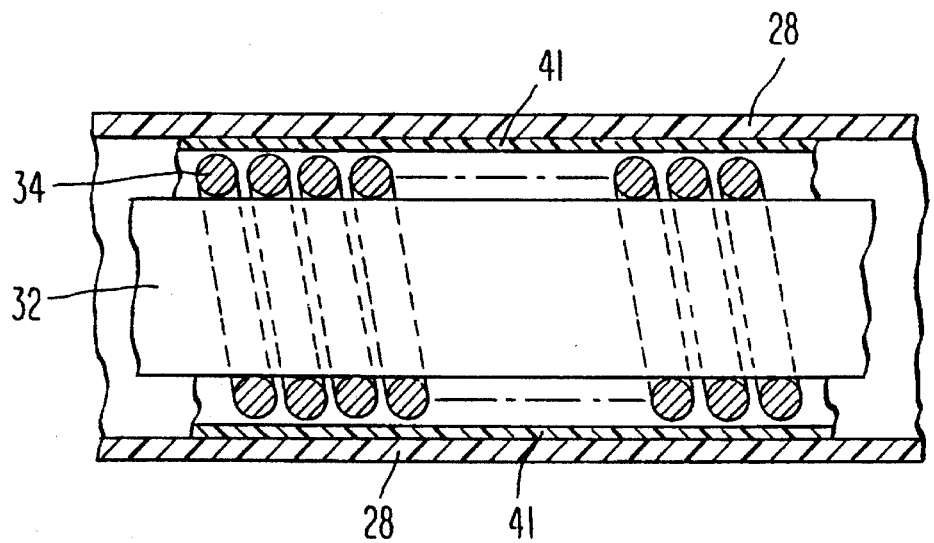
FIG. 5 is a diagrammatic cross-sectional view of another embodiment of this invention wherein a flexible thin-walled tube is interference fit with the ID of the lead tubing, illustrated together with a stylet providing a minimum clearance between the OD of the stylet and the ID of the coil.

Referring now to FIG. 5, there is shown another embodiment of the lead of this invention. In this arrangement, a thin tube 41, suitably polyamide, is placed just inside the ID of the casing 28. The tube 41 has an OD relative to the ID of casing 28 such that tube 41 is interference fit with casing 28. Tube 41 has a thickness so as to provide minimum clearance with coil 34, to prevent any outward expansion of the coil, i.e., to increase stiffness. Also, suitably, a stylet 32 is placed within the coil lumen 33, the stylet having an OD which is about the same as the coil ID. In this manner, the combination of tube 41 and stylet 32 holds the coil stiff by preventing either increase of its OD or decrease of its ID. Also, as with the other embodiments, the material of tube 41 is chosen to decrease the friction between the coil 34 and the tube casing. For an application where it is desired to rotate the entire lead, including the casing, the material is chosen to maintain a high friction.

From the embodiments of the invention as discussed above, it is seen that there is provided a pacing lead having an improved combination of flexibility at the proximal and distal lengths where relative flexibility is needed, and relative stiffness through a mid-section or intermediate length, where flexibility is not as necessary, thereby providing improved torsion characteristics.

What is claimed is:

1. A pacing lead having a proximal end for connection to a pacemaker, a distal end, a substantially cylindrical lead length between said ends, said length having an outer tubing, an electrode at about the distal end thereof, a distal element at said distal end, and connecting means along said lead length for providing an electrical connection from said proximal end to said electrode and a mechanical connection from said proximal end to said distal element, said connecting means having a stiffness, further comprising stiffening means extending a predetermined intermediate length of about 28–36 cm intermediate of said proximal and distal ends for providing a stiffness to said connecting means which is relatively greater through said intermediate length than is the stiffness of said connecting means proximal to and distal from said intermediate length.

2. The pacing lead as described in claim 1, wherein said connecting means comprises a conductor coil having an outside and an inner diameter, said distal element comprising a rotatable element connected to said conductor coil at said distal end, whereby a rotational force imparted to said conductor coil causes rotation of said distal element.

3. The pacing lead as described in claim 2, wherein said stiffening means comprises an intermediate tubing extending through said intermediate length, said intermediate tubing being interference fit within the inside of said outer tubing and spaced close to said conductive coil.

4. The pacing lead as described in claim 2, in combination with a stylet inserted within said conductor coil, said stylet having an outer diameter substantially the same as said inner diameter of said conductor coil.

5. The pacing lead as described in claim 2, wherein said stiffening means is positioned between said conductor coil outside and said outer tubing, said stiffening means comprising a low friction material.

6. The pacing lead as described in claim 5, wherein said stiffening means is a polyamide tubing.

7. The pacing lead as described in claim 2, wherein said conductor coil is a multiple filar wire, and said stiffening means comprises a coating covering the outside surface of said filars throughout said intermediate length.

8. The pacing lead as described in claim 1, wherein said distal element comprises fixation means for fixing said lead distal end to a patient's heart wall.

9. The pacing lead as described in claim 1, comprising a low friction shrink tubing between said outer tubing and said connecting means and extending only through said intermediate length.

10. The pacing lead as described in claim 1, wherein said lead length is about 60 cm and said intermediate length is in the range of 28–30 cm.

11. A body implantable lead of the type including a proximal end adapted to be manipulated and a distal end adapted to contact living tissue, said lead having a conductor extending between said proximal and distal ends, said lead comprising a first proximal segment of at least 10 cm extending a first distance from said proximal end toward said distal end, a distal segment of at least 10 cm extending a second distance from said distal end proximal toward said proximal end, and an intermediate segment of at least 28 cm extending for an intermediate distance between said proximal and said distal segments, said lead having a casing extending the length of said lead from said proximal end to said distal end, said intermediate segment further comprising stiffness means interposed between said conductor and said casing for imparting a greater stiffness to said conductor throughout said intermediate segment relative to said proximal and distal segments.

12. The lead as described in claim 11, further comprising a movable distal element positioned at about said distal end and connected mechanically to said conductor, a proximal element at said proximal end to which rotational torque can be applied, said conductor being connected to said proximal element at said proximal end and said distal element at said distal end, whereby rotational torque applied to said proximal element is transmitted through said conductor to said distal element.

13. The lead as described in claim 11, wherein said conductor is a coil, and wherein said stiffness means comprises an element of low friction, whereby the friction between said low friction element and said casing is less than the friction between said coil and said casing in said proximal and distal segments.

14. The lead as described in claim 13, wherein said low friction element is a covering over said coil.

15. A pacing lead for use in a pacing system, having a proximal end for connection to a pacemaker and a distal end having at least one electrode for interaction with a patient's heart, said lead having a length from said proximal end to said distal end and a coil conductor running substantially said length to transmit electrical signals between said pacemaker and said electrode, said coil conductor having a torsional stiffness throughout said length, and a substantially cylindrical outer casing extending substantially said length of said lead, comprising intermediate means extending only for an intermediate length of said lead for imparting increased torsional stiffness to said coil conductor relative to the remaining lengths of said lead at the proximal and distal ends, wherein said coil has a coil conductor outside and a coil diameter, and said intermediate means is adhered closely to said outside so as to constrain variation in said coil diameter, and further wherein said intermediate means is made of a low friction material so as to reduce transmission of torsion from said coil conductor to said casing.

16. The pacing lead as described in claim 15, wherein said intermediate means comprises a tubing.

* * * * *